United States Patent

Kawai et al.

Patent Number: 5,417,572
Date of Patent: May 23, 1995

[54] METHOD FOR EXTRACTING A MARGIN LINE FOR DESIGNING AN ARTIFICIAL CROWN

[75] Inventors: Masaharu Kawai, Kanagawa; Katsuya Miyoshi, Tokyo; Masami Baba, Saitama, all of Japan

[73] Assignee: Nikon Corporation, Tokyo, Japan

[21] Appl. No.: 312,678

[22] Filed: Sep. 28, 1994

Related U.S. Application Data

[63] Continuation of Ser. No. 32,248, Mar. 17, 1993, abandoned.

[30] Foreign Application Priority Data

Mar. 23, 1992 [JP] Japan ................... 4-065091

[51] Int. Cl.$^6$ ............................. A61C 5/08
[52] U.S. Cl. .................... 433/218; 433/213
[58] Field of Search .............. 433/202.1, 213, 215, 433/218, 223; 364/413.28; 33/513, 514

[56] References Cited

U.S. PATENT DOCUMENTS

| | | | |
|---|---|---|---|
| 4,575,805 | 3/1986 | Moermann et al. | 433/223 |
| 4,663,720 | 5/1987 | Duret et al. | 364/413.28 |
| 4,952,149 | 8/1990 | Duret et al. | 433/215 |
| 4,964,770 | 10/1990 | Steinbichler | 433/223 |
| 5,092,022 | 3/1992 | Duret | 433/213 |

FOREIGN PATENT DOCUMENTS

| | | |
|---|---|---|
| 0441359 | 8/1991 | European Pat. Off. |
| 0473476 | 3/1992 | European Pat. Off. |
| 2210707 | 6/1989 | United Kingdom |
| 9115163 | 10/1991 | WIPO ................ 433/223 |

OTHER PUBLICATIONS

Montavalli, Saeid et al, "A Part Image Reconstruction System for Reverse Engineering of Design Modifications", *Journal of Manufacturing Systems*, vol. 5, No. 10, 1991, pp. 383–395.

Primary Examiner—Cary E. O'Connor
Attorney, Agent, or Firm—Shapiro and Shapiro

[57] ABSTRACT

Amounts of variation of data representing the shape of an abutment tooth are determined, and a train of points is extracted from the amounts of variation. Then a developed view of the surface shape of the abutment tooth is displayed, and the obtained train of points is also displayed in the developed view. The margin line for designing the artificial crown is determined, based on thus displayed train of points.

13 Claims, 3 Drawing Sheets

RADIX DENTIS

METHOD FOR EXTRACTING A MARGIN LINE FOR DESIGNING AN ARTIFICIAL CROWN

This is a continuation of application Ser. No. 08/032,248 filed Mar. 17, 1993, now abandoned.

BACKGROUND OF THE INVENTION

1. Field of the Invention

The present invention relates to a method for extracting the margin line for the designing of an artificial crown, which is used for complementing the defective part of a defective tooth.

2. Related Background Art

Conventionally, an artificial crown has been prepared by a manual process called waxing-up method, as shown in FIGS. 6A to 6C. At first a plaster cast of the abutment tooth, as shown in FIG. 6A, is prepared. The dentist forms the abutment tooth by shaping the diseased part, and said plaster cast is prepared from an impression of said abutment tooth. Then a margin line 61 is drawn on said plaster cast of the abutment tooth. The position of said margin line is determined by the dental technician, who observes the plaster cast and attaches marks where he thinks the margin line exists. Subsequently, as shown in FIG. 6B, molten wax is heaped on the plaster cast of the abutment tooth in such a manner that the wax does not overflow the margin line to the side of the plaster cast of the abutment tooth and that the wax is smoothly shaped in the vicinity of the margin line. In this manner the shape of the artificial crown is prepared as shown in FIG. 6C. An impression is prepared by thus prepared model of the artificial crown, and the artificial crown is prepared by said impression.

In such conventional method, the determination of the margin line depends greatly on the skill of the technician. An inadequate margin between the abutment tooth and the artificial crown leads to the detachment of the artificial crown or to the dental caries inside the artificial crown. Also such inadequate margin requires additional adjustment by the dentist at the attachment of the artificial crown to the diseased part, thus necessitating a longer time of treatment.

The preparation of the artificial crown, which has been manually conducted up to now, will surely depend upon CAD/CAM (computer aided design/computer aided manufacturing) in the near future.

SUMMARY OF THE INVENTION

In anticipation of the CAD/CAM preparation of the artificial crown in the near future, the object of the present invention is to provide a method for extracting the margin line, capable of easy determination thereof.

The method of the present invention, for extracting the margin line at the designating of the artificial crown, comprises steps of:

(a) determining the amounts of variation of the data representing the shape of the abutment tooth;
(b) extracting a train of points that can be identified as a margin area, from said amounts of variation; and
(c) determining the margin line based on said train of points.

The above-mentioned method allows determination of a train of points that can be identified as the margin area by calculation. Also the margin line can be easily determined by plotting said train of points on a development view of the surface.

DETAILED DESCRIPTION OF THE PREFERRED EMBODIMENTS

Now the present invention will be explained in detail with reference to a preferred embodiment thereof.

At first, the shape of a plaster cast of the abutment tooth, prepared in the same manner as in the conventional art, is measured to obtain shape data of said abutment tooth. Said measurement can be achieved by a known technology, such as by CT scanning or by a three-dimensional measuring instrument. Thus the data indicating the three-dimensional shape of the abutment tooth are obtained from the measurement data.

Figure 2A:
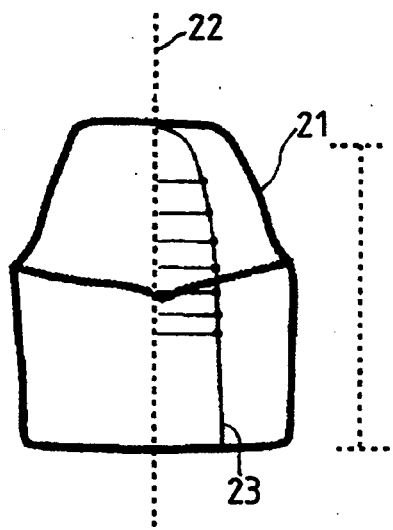
FIGS. 2A and 2B are views showing a calculation method for determining the train of points of the margin area and a method for preparing a development view in an embodiment of the margin line extracting method of the present invention.

A train of points in the margin area is extracted from said data representing the three-dimensional shape of the abutment tooth, for example, by a method explained in the following:

(1) At first, as shown in FIG. 2A, a central axis 22 of the three-dimensional shape 21 of the abutment tooth is determined:

(2) There is considered a crossing line between a surfaces including the central axis 22 and a curved plane constituting the shape 21 of the abutment tooth. In FIG. 2A, a line 23 corresponds to said crossing line. Then calculated is the distance between the central axis 22 and each point on said crossing line 23, contained in the curved surface constituting the abutment tooth 21. Then the inclination Si between the adjacent points is determined for each point i on the crossing line 23 in the following manner:

$$Si = Ij - (j = i + 1)$$

wherein Si is the inclination, and Ii is the distance from the central axis.

(3) Based on the above-explained calculation, the margin area is defined at a point where the inclination crosses zero or where the variation of the inclination exceeds a certain value. More specifically, the margin area is defined at a point j satisfying:

$$Si \cdot Sj < 0,$$

or $$|a| \gtreqless \text{constant}, a = Sj + Si$$

in which a represents the amount of variation of the inclination.

The margin area can be extracted in the above-explained manner. The foregoing explanation is limited to the calculation on the crossing line 23, but there can be selected plural planes containing the central axis 22. Consequently a train of points can be obtained by effecting the above-explained calculation on the crossing line corresponding to each plane.

Figure 1A:
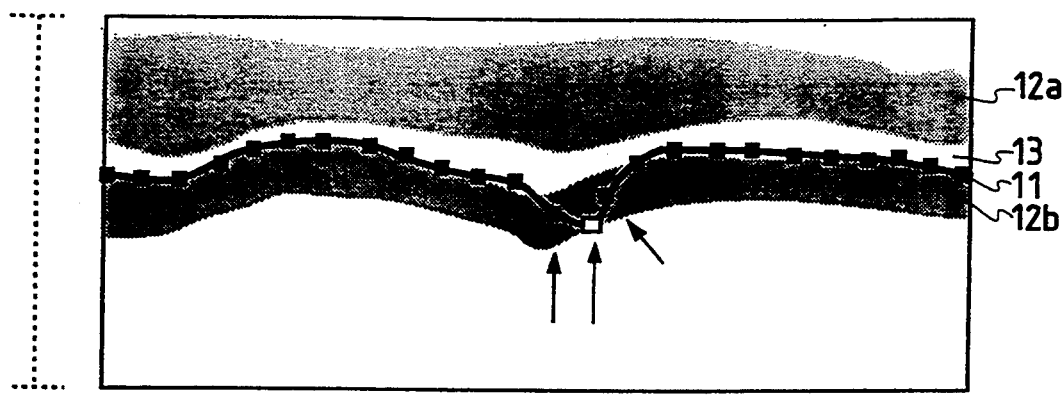
FIGS. 1A and 1B are views showing display states of the train of points in an embodiment of the margin line extracting method of the present invention.
Figure 2B:
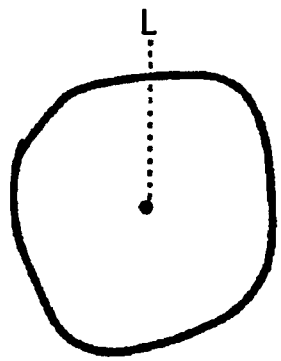

Then the train of points representing the margin area, determined in the above-explained manner, is displayed on a display unit. In this state, a development view of the shape of the abutment tooth is displayed, and said point train of the margin area is superposedly displayed. Said development view is obtained by developing the lateral surface of the three-dimensional shape of the abutment tooth and displaying said lateral surface in planar form. More specifically the developed data of the abutment tooth are prepared by developing the cylindrical surface from a broken line L shown in FIG. 2B, and the development view is displayed, based on said developed data. The train of points representing the margin area is displayed on the corresponding position on said development view. FIG. 1A shows the display of said point train of the margin area on the developed view, wherein said points are connected by straight lines, and such connection can be made by hitting the points with a mouse.

The development view can be displayed in a shaded display or a bent-line display as if seen from an oblique direction, selectively by a menu. FIG. 1A illustrates the shaded display.

Subsequently there is executed a correction operation for the point train of the margin area extracted by calculation and the lines connecting the points. Said correction is conducted by hitting a displayed point and moving said point by giving an amount of variation by keys or a dial.

Said correction operation will be explained in the following, with reference to FIG. 1A, in which shaded areas 12a, 12b slope gradually upward to an area 13. The area 13 constitutes a ridge line of a rise. The actual margin line is considered present in the vicinity of the peak of the rise in the developed view, namely in the area 13 in FIG. 1A. The point train 11 in FIG. 1A indicates the margin area determined by the aforementioned calculation. Most of the points of the train 11 are in the area 13, and can be considered close to the actual margin line. The points indicated by arrows are in the area 12b, namely on the sloped portion. These points, are considered deviated from the actual margin line, having been improperly obtained by the aforementioned calculation method, and have to be corrected in their positions. As explained above, the correction can be achieved by hitting a point to be corrected with a mouse and moving said point to a desired position by setting the amount of movement, for example by keys or a dial.

Figure 5:
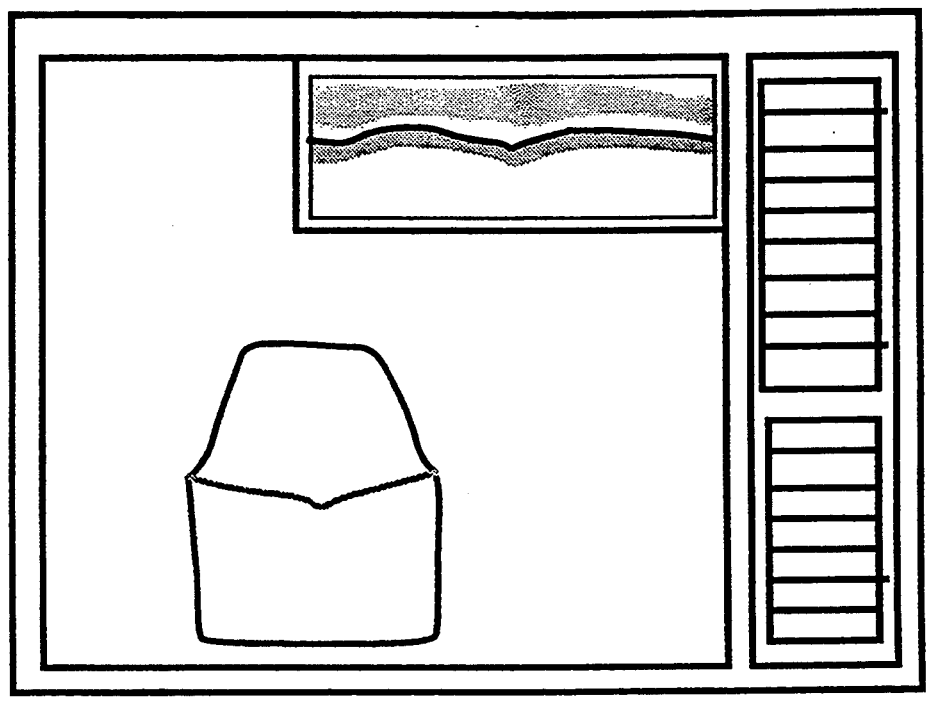
FIG. 5 is a view, showing a three-dimensional shape and a development view, both shown in a display device, in an embodiment of the margin line extracting method of the present invention.
Figure 6A:
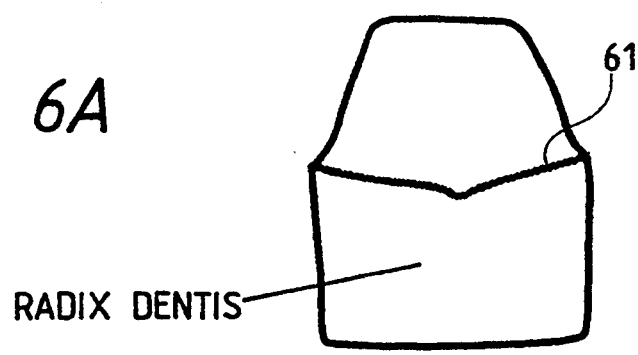
FIGS. 6A to 6C are views showing the steps of preparation of an artificial crown by the waxing-up method.
Figure 6B:
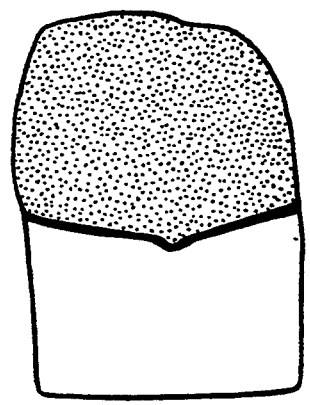
Figure 6C:
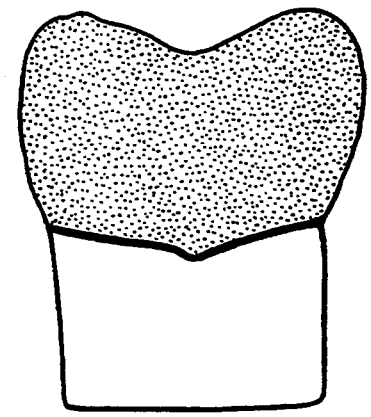

The developed view of the abutment tooth and the three-dimensional shape thereof can be simultaneously displayed as shown in FIG. 5, wherein in addition to the display of the three-dimensional shape of the abutment tooth, the developed view is displayed in the upper part. The point train and the connecting lines, representing the margin area, can be displayed both in the three-dimensional shape and in the developed view. The above-mentioned correcting operation for the points may be conducted on the display of the three-dimensional shape, but is more easily conducted on the two-dimensional developed view.

The amount of movement of the point for correction is reflected both on the developed data and on the three-dimensional data. Consequently, when the point is moved on the developed view, the corresponding point in the display of the three-dimensional shape may also be moved in corresponding manner.

Figure 3:
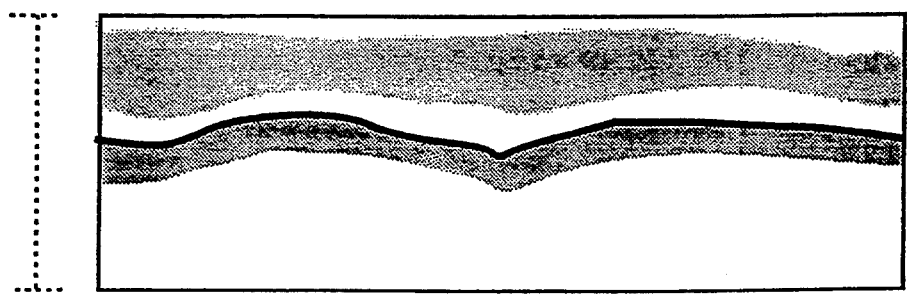
FIG. 3 is a development view with shaded display, in an embodiment of the margin line extracting method of the present invention.
Figure 4:
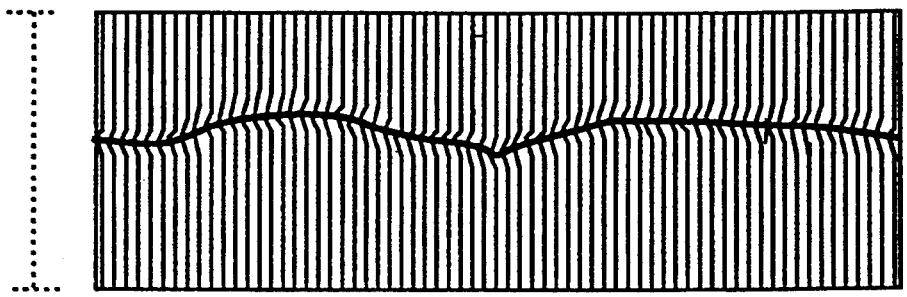
FIG. 4 is a development view with line display in an embodiment of the margin line extracting method of the present invention.

After the points are corrected in position, they are again connected with straight lines. FIG. 3 shows a state in which the corrected points are again connected by the lines, and FIG. 4 shows a bent line display corresponding to the state shown in FIG. 3. Of course, a display as shown in FIG. 4 may be employed for the correction of point positions, instead of the display as shown in FIG. 1A.

Figure 1B:

The point train thus determined is converted into three-dimensional data, and formed as a curve as shown in FIG. 1B, and this curve corresponds to the margin line. Said margin line is registered in the shape data of the abutment tooth.

The designing of the artificial crown can be made based on the shape data of the abutment tooth, in which thus determined margin line is registered. The margin line of the artificial crown to be designed can be made to coincide with the margin line registered in said shape data of the abutment tooth.

As explained in the foregoing, the present invention simplifies the extraction of the margin line in the designing of dental complement. As a result it is rendered possible to reduce the designing time and to improve productivity.

Also the dental complement provides an improved durability, since the accuracy of the margin line is improved in comparison with that in the prior art.

What is claimed is:

1. A method for extracting the margin line in the designing of an artificial crown, comprising steps of:
    obtaining data representing the shape of an abutment tooth;
        determining amounts of variation of the data representing the shape of the abutment tooth;
        extracting a train of points which can be identified as a margin area, from said amounts of variation;
        displaying said train of extracted points; and
        determining the margin line based on said displayed train of points.

2. A method according to claim 1, further comprising a step of displaying a developed view of the surface shape of said abutment tooth and displaying said train of points in said developed view.

3. A method according to claim 2, further comprising a step of connecting said points with straight lines.

4. A method according to claim 3, wherein the margin line is determined by adjusting positions of points in said train and connecting the points in said train again with straight lines in the display.

5. A method according to claim 2, wherein said developed view of the surface shape of the abutment tooth is displayed in shaded representation.

6. A method according to claim 2, further comprising a step of displaying the three-dimensional shape of said abutment tooth and also displaying said train of points on said display of the three-dimensional shape.

7. A method according to claim 6, wherein a movement of a point in said train displayed in said developed view of the surface shape causes a movement of the point of the train displayed in said three-dimensional shape.

8. A method according to claim 1, further comprising a step of converting said train of points into three-dimensional data.

9. A method according to claim 8, further comprising a step of registering the train of points, converted into said three-dimensional data, in the shape data of said abutment tooth.

10. A method according to claim 1, further comprising a step of connecting said points with straight lines.

11. A method according to claim 10, wherein the margin line is determined by adjusting positions of points in said train and connecting the points in said train again with straight lines in the display.

12. A method according to claim 1, further comprising a step of displaying the three-dimensional shape of said abutment tooth and also displaying said train of points on said display of the three-dimensional shape.

13. A method according to claim 12, wherein a movement of a point in said train causes a movement of the point of the train displayed in said three-dimensional shape.

* * * * *